(12) United States Patent
Aimiya et al.

(10) Patent No.: US 9,023,659 B2
(45) Date of Patent: May 5, 2015

(54) SILICA NANOPARTICLE EMBEDDING QUANTUM DOTS, PREPARATION METHOD THEREOF AND BIOSUBSTANCE LABELING AGENT BY USE THEREOF

(75) Inventors: Takuji Aimiya, Tokyo (JP); Masaru Takahashi, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 636 days.

(21) Appl. No.: 13/318,177

(22) PCT Filed: Mar. 1, 2010

(86) PCT No.: PCT/JP2010/053220
§ 371 (c)(1),
(2), (4) Date: Oct. 31, 2011

(87) PCT Pub. No.: WO2010/128604
PCT Pub. Date: Nov. 11, 2010

(65) Prior Publication Data
US 2012/0045850 A1   Feb. 23, 2012

(30) Foreign Application Priority Data

May 8, 2009   (JP) ................................. 2009-113389

(51) Int. Cl.
| | | |
|---|---|---|
| *G01N 33/552* | (2006.01) | |
| *C01B 33/18* | (2006.01) | |
| *B82Y 15/00* | (2011.01) | |
| *G01N 33/58* | (2006.01) | |
| *C09K 11/02* | (2006.01) | |
| *C09K 11/59* | (2006.01) | |
| *C09K 11/62* | (2006.01) | |

(52) U.S. Cl.
CPC ................. *C01B 33/18* (2013.01); *B82Y 15/00* (2013.01); *G01N 33/588* (2013.01); *C09K 11/02* (2013.01); *C09K 11/59* (2013.01); *C09K 11/62* (2013.01); *Y10S 977/773* (2013.01); *Y10S 977/779* (2013.01)

(58) Field of Classification Search
None
See application file for complete search history.

(56) References Cited

U.S. PATENT DOCUMENTS

| | | | | |
|---|---|---|---|---|
| 7,648,845 | B2 * | 1/2010 | Nie et al. | 436/535 |
| 8,164,074 | B2 * | 4/2012 | Boyden et al. | 250/492.1 |
| 2009/0169861 | A1 * | 7/2009 | Nie et al. | 428/315.5 |

FOREIGN PATENT DOCUMENTS

| | | |
|---|---|---|
| JP | 2003-206475 | 7/2003 |
| JP | 2003-321226 | 11/2003 |
| JP | 2003-329686 | 11/2003 |
| JP | 2005-281019 | 10/2005 |
| WO | 2007-034877 | 3/2007 |
| WO | 2007-138851 | 12/2007 |
| WO | WO 2008-032618 | 3/2008 |

OTHER PUBLICATIONS

Sathe et al, "Mesoporous Silica Beads Embedded with Semiconductor Quantum Dots and Iron Oxide Nanocrystals: Dual-Function Microcarriers for Optical Encoding and Magnetic Separation", Anal. Chem., 2006, 78, 5627-5632.*
Letant, "Study of porous glass doped with quantum dots or laser dyaes under alpha irradiation", Applied Physics Letters, 2006, 88, 103110.*
Japanese Office Action, Notification of Reasons for Refusal, Patent Application No. JP 2011-512318, Mailing Date: May 7, 2014 (4 pages)
English translation of Japanese Office Action, Notification of Reasons for Refusal, Patent Application No. JP 2011-512318, Mailing Date: May 7, 2014 (4 pages).

* cited by examiner

*Primary Examiner* — Chris L Chin
(74) *Attorney, Agent, or Firm* — Lucas & Mercanti, LLP

(57) ABSTRACT

Disclosed is a quantum dot-embedded silica nanoparticle having plural quantum dots embedded within the silica nanoparticle, wherein the number of quantum dots existing in a concentric area within 10% of a radius from a center of the silica nanoparticle accounts for 10 to 70% of the number of total quantum dots embedded in the silica nanoparticle.

16 Claims, No Drawings

SILICA NANOPARTICLE EMBEDDING QUANTUM DOTS, PREPARATION METHOD THEREOF AND BIOSUBSTANCE LABELING AGENT BY USE THEREOF

This Application is a 371 of PCT/JP2010/053220 filed Mar. 1, 2010 which, in turn, claimed the priority of Japanese Patent Application No. 2009-113389 filed May 8, 2009, both applications are incorporated by reference herein.

TECHNICAL FIELD

The present invention relates to a high-luminous, quantum dot-embedding silica nanoparticle which embeds plural quantum dots within the silica particle, a preparation method of the same, and a biosubstance labeling agent by use of the same.

TECHNICAL BACKGROUND

It is well known that, among semiconductor nanoparticles, nano-sized particles having a smaller particle size than an electron wavelength (approximately, 10 nm) are greatly affected by the finite nature of particle size on the motion of an electron, as a quantum size effect and exhibit specific physical properties differing from its bulk body. A semiconductor nanoparticle which is composed of a nanometer-sized semiconductor material and exhibits a quantum confinement effect is generally called a quantum dot. Such a quantum dot, which is a small agglomerate of some ten nms and composed of some hundreds to some thousands of semiconductor atoms, emits an energy equivalent to the energy band gap of the quantum dot when absorbing light from an exciting source and reaching an energy-excited state.

Accordingly, it is known that a quantum dot exhibits unique optical characteristics through a quantum size effect. Specifically, a quantum dot exhibits characteristics such that (1) control of particle size renders it feasible to emit light of various wavelengths or colors, (2) it is possible to allow particles of various sizes and exhibiting a broad absorption band to emit light by the exciting light of a single wavelength, (3) a fluorescence spectrum exhibiting a favorable symmetrical form, and (4) it exhibits enhanced durability and excellent fade resistance, compared to organic dyes.

On the other hand, there has been noted in vivo light imaging for small animals and optical system devices which are capable of externally observing cells within the living body of a small animal without injuring the living body (non-operatively) have been commercially available from various manufacturers. This is a method in which a labeled fluorescent material capable of selectively gathering at a site to be observed within a living body is injected into the living body and is externally exposed to exciting light and the emitted light is externally monitored. There has been studied a technique of employing, as a means for labeling a biomaterial, a biomaterial labeling agent of a molecular labeling substance being attached to a marker substance.

Recently, there has been noted a technique of employing a quantum dot as the foregoing marker substance. For instance, there has been studied a biomaterial labeling agent in which a polymer having a polar functional group is physically and/or chemically attached to the surface of a quantum dot (as described in, for example, patent document 1).

Recently, there have been desired biomaterial labeling agents exhibiting enhanced emission intensity to perform high-sensitive biomaterial detection. As one of them was disclosed a method of allowing plural quantum dots to be embedded within a silica nanoparticle (as described in, for example, patent documents 2 and 3).

However, it was proved that, when a quantum dot-embedded silica was prepared in accordance with the method disclosed in the patent document 2 by the inventors of the present invention and its emission intensity was measured, the emission intensity was lower than that expected from the number of quantum dots, requiring an additional improvement.

Further, the method disclosed in the patent document 3 employed a nonionic surfactant in the preparation process. Such a nonionic surfactant possibly causes denaturation of a biomaterial and in cases when using a quantum dot-embedded silica, it was necessary to require a step for removing such a surfactant, producing industrial problems.

PRIOR ART DOCUMENT

Patent Document

Patent document 1; JP 2003-329686 A
Patent document 2; JP 2003-321226 A
Patent document 3; WO 2007/034877 A1

SUMMARY OF THE INVENTION

Problems to be Solved

The present invention has come into being in view of the foregoing problems and circumstances and it is an object of the present invention to provide high-luminance silica nanoparticles with embedded quantum dots and a preparation method of the same. It is also an object of the invention to provide a biomaterial labeling agent by use of the same.

Means for Solving the Problems

As a result of extensive study by the inventors to solve the foregoing problems, it was found that quantum dot-embedded silica nanoparticles obtained by the methods known in the art resulted in a lowering of emission intensity, which was caused by quantum dots being concentrated in the central portion of a silica nanoparticle. It was further found that plural quantum dots were dispersed over the whole within the particle, whereby quantum dot-embedded silica nanoparticles of enhanced luminance and a biosubstance labeling agent by use of the same were achieved, leading to the present invention.

Thus, the above-described problems related to the present invention were solved by the following constitution:

1. A quantum dot-embedded silica nanoparticle having plural quantum dots embedded within the nanoparticle, wherein the number of quantum dots existing in a concentric area within 10% of a radius from a center of the silica nanoparticle accounts for 10 to 70% of total quantum dots embedded in the silica nanoparticle.

2. The quantum dot-embedded silica nanoparticle, as described in the foregoing 1, wherein the number of quantum dots existing in a concentric area within 10% of a radius from a center of the silica nanoparticle accounts for 30 to 50% of total quantum dots embedded in the silica nanoparticle.

3. The quantum dot-embedded silica nanoparticle, as described in the foregoing 1 or 2, wherein the quantum dot comprises any one of a II-VI group compound, a III-V group compound and a IV group element.

4. The quantum dot-embedded silica nanoparticle, as described in any one of the foregoing 1 to 3, wherein the quantum dot comprises InP or InGaP.

5. The quantum dot-embedded silica nanoparticle, as described in any one of the foregoing 1 to 4, wherein the quantum dot comprises Si.

6. The quantum dot-embedded silica nanoparticle, as described in any one of the foregoing 1 to 5, wherein the surface thereof is modified with an organic molecule.

7. A method of producing a quantum dot-embedded silica nanoparticle, as described in the foregoing 1 to 5, the method comprising the steps of:

(a) mixing a silicon-containing alkoxide compound and quantum dots to prepare a quantum dot-containing solution, (b) mixing an organic solvent, water and a base to prepare a mixture, and (c) dividing the quantum dot-containing solution prepared in the step (a) to parts and adding each of the parts intermittently to the mixture prepared in the step (b) with stirring to be reacted.

8. A biosubstance labeling agent, wherein a quantum dot-embedded silica nanoparticle, as described in any one of the foregoing 1 to 6, is combined with a molecular labeling material through an organic molecule.

Effect of the Invention

According to the present invention, there can be provided silica nanoparticles having quantum dots embedded therein and exhibiting enhanced luminance, and a production method thereof. There can also be provided a biosubstance labeling agent by using the same.

EMBODIMENTS OF THE INVENTION

The present invention is featured in a quantum dot-embedded silica nanoparticle having plural quantum dots embedded in the nanoparticle, wherein the number of quantum dots existing in a concentric area within 10% of a radius from the center of the silica nanoparticle accounts for 10 to 70% of the total quantum dots embedded in the silica nanoparticle. This feature is a technical feature in common with the invention related to the foregoing embodiments 1 to 8.

In one preferred embodiment of the present invention, the number of quantum dots existing in the concentric area within 10% of the radius from the center of the silica nanoparticle accounts for 30 to 50% of the total quantum dots embedded in the silica nanoparticle to achieve effects of the present invention.

Further, in one preferred embodiment of the present invention, the quantum dot comprises any one of a II-VI group compound, a III-V group compound and a IV group element. In that case, the quantum dot preferably comprises InP or InGaP. Further, the quantum dot preferably comprises Si. Furthermore, in the silica nanoparticle having quantum dots embedded therein, the surface of the particle is preferably modified with an organic molecule.

In the embodiments of the present invention, the method of producing the quantum dot-embedded silica nanoparticles preferably comprises the steps of (a) to (c), as afore-described.

The quantum dot-embedded silica nanoparticle of the present invention is usable as a biosubstance labeling agent in which the quantum dot-embedded silica nanoparticle and a molecular labeling material are combined through an organic molecule.

In the following, there will be detailed the present invention and its constituent elements and preferred embodiments of the invention.

Production Method of Silica Nanoparticle:

Silica nanoparticles are produced preferably by a method, a so-called Stoeber method, as described in, for example, Journal of Colloid Science, vol. 26, page 62 (1968), in which a silicon-containing alkoxide compound, such as tetraethoxysilane, is hydrolyzed under an alkaline condition using ammonia water. The particles size can be freely controlled by applying commonly known reaction conditions such as an addition quantity of water, ethanol, alkali or the like, whereby an average particle size of 30 to 800 nm can be achieved. A coefficient of variation indicating dispersion of particle size can be controlled so as to fall within a range of not more than 20%.

In the present invention, the average particle size was determined in the manner that particles are photographed by using a scanning electron microscope (SEM) and the sectional area is measured value with respect to a sufficient number of particles, in which the diameter of a circle having an area equivalent to the measured is determined as the particle size. A coefficient of variation is defined as a value calculated from the particle size distribution of 1,000 particles.

Production Method of Quantum Dot-Embedded Silica Nanoparticle:

The production method of quantum dot-embedded silica nanoparticles of the present invention may employ various embodiments of the method and is not specifically restricted but basically the production method preferably comprises at least steps (a) to (c), described below:

(a) mixing a silicon-containing alkoxide compound and quantum dots to prepare a quantum dot-containing solution, (b) mixing an organic solvent, water and a base to prepare a mixed solution, and (c) dividing the quantum dot-containing solution prepared in the foregoing step (a) and intermittently adding it to the mixed solution prepared in the foregoing step (b) to perform reaction.

The foregoing method is featured in that, when preparing silica nanoparticles by the Stoeber method, a silicon-containing alkoxide compound such as ethoxysilane and quantum dots are mixed in advance and the mixed solution is intermittently added thereto.

In the following, the production steps of quantum dot-embedded silica nanoparticles of the present invention will be further described in detail.

Step (1): mixing a silicon-containing alkoxide compound such as tetraethoxysilane and quantum dots, Step (2): mixing an organic solvent such as ethanol, water and a base to prepare a mixed solution, Step (3): adding a quantum dot-containing solution prepared in the step (1) intermittently to the mixed solution prepared in the step (2) with stirring to promote a reaction, Step (4): recovering the formed quantum dot-embedding silica nanoparticles from the reaction mixture through filtration or centrifugal separation, Step (5): modifying the quantum dot-embedding silica nanoparticles obtained in the step (4) with an organic molecule, Step (6): allowing the quantum dot-embedding silica nanoparticles which were modified with an organic molecule in the step (5) to combine it with a molecular labeling substance to obtain a biosubstance labeling agent.

Examples of a silicon-containing alkoxide compound obtained in the step (1) include a tetraalkoxysilane such as tetraethoxysilane or tetramethoxysilane; and a trialkoxysilane compound such as methyltrimethoxysilane, methyltriethoxysilane and phenyltriethoxysilane. There are also cited a silicon-containing alkoxide compound containing an organic functional group. Specific examples thereof include mercaptopropyltriethoxysilane and aminopropyltriethoxysilane.

Such silicon-containing alkoxide compounds may be used singly or in combination of two or more.

Quantum dots for use in the quantum dot-embedded silica nanoparticles of the present invention preferably are those which have an average particle size of 2 to 10 nm and emit visible to near-infrared light within the wavelength of 400 to 900 nm when excited by ultraviolet to near-infrared light within the wavelength of 200 to 700 nm.

The foregoing quantum dot can employ any one of a quantum dot containing, as a component, a II-VI group compound, a III-V group compound or a IV group element (which are also called "II-VI group dot", "III-V group quantum dot, and IV group quantum dot, respectively).

Specific examples thereof include CdSe, CdS, CdTe, ZnSe, ZnS, ZnTe, InP, InN, InAs, InGaP, GaP and GaAs.

There can also be used a quantum dot in which the foregoing quantum dot is used as a core and further thereon, a shell is provided. In the present specification, a quantum dot having a shell is denoted as CdSe/ZnS in the case of a CdSe core and a ZnS shell. Examples thereof include CdSe/ZnS, CdS/ZnS, InP/ZnS, InGaP/ZnS, Si/SiO$_2$, Si/ZnS, Ge/GeO$_2$ and Ge/ZnS, but are not limited to these.

The quantum dot may optionally be surface-treated with an organic polymer or the like. Examples thereof include CdSe/ZnS containing a carboxyl group on the surface (produced by Invitrogen Corp.) and CdSe/ZnS containing an amino group on the surface (produced by Invitrogen Corp.).

A III-V group quantum dot preferably employs InP, InN, InGaP, InP/ZnS and InGaP/ZnS. Of these, a quantum dot having a core of InP or InGaP which exhibits enhanced emission intensity is specifically preferred.

A IV group quantum dot preferably employs Si, Si/SiO$_2$, Si/ZnS, Ge, Ge/GeO$_2$, and Ge/ZnS. Of these, a quantum dot having a core of Si which exhibits an enhanced emission intensity is specifically preferred.

A mixing ratio of silicon-containing alkoxide compound to quantum dot is not specifically limited but it is preferred to mix quantum dots so that the finally obtained silica nanoparticles contain quantum dots in a concentration of $1 \times 10^{-6}$ to $1 \times 10^{-2}$ mol/L. An extremely low concentration cannot achieve sufficient fluorescence. Whereas, an extremely high concentration causes concentration quenching, even if uniform dispersion in silica is achieved.

An organic solvent used in the step (2) may be any one which is usable for hydrolysis of a usual silicon-containing alkoxide compound and examples thereof include methanol, ethanol, tetrahydrofuran, dimethylformamide and dimethylsulfoamide, which may be used singly or in combination.

A base used in the step (2) may be any one which is usable for hydrolysis of a usual silicon-containing alkoxide compound and example thereof include ammonia, sodium hydroxide, and potassium hydroxide, which may be used as an aqueous solution.

In a case when using tetraethoxysilane as a silicon-containing alkoxide compound, ethanol as an organic solvent and aqueous ammonia as a base, the molar ratio of the individual compound to be fed is as follows. In the case when using 1 mole of tetraethoxysilane, "a" mol of ethanol, "r" mol of water and "b" mol of ammonia, they are mixed in "a" of 20 to 400, "r" of 10 to 200, and "b" of 10 to 40. Specifically, there are applicable conditions described in the afore-described non-patent document [Journal of Colloid Science, vol. 26, page 62 (1968)].

In the step (3), the reaction temperature, which may be a condition applicable to hydrolysis of conventional silicon-containing alkoxide compounds, is from room temperature to 50° C.

Intermittent addition of a quantum dot-containing solution is not technically limited but can be conducted by using a syringe pump or a dropping funnel.

The total addition amount is divided into 2 to 30 parts, preferably 3 to 20 parts and more preferably 5 to 10 parts; and addition can be conducted at intervals of 1 to 120 minutes, preferably 3 to 90 minutes, and more preferably 5 to 60 minutes.

Optimization of the divided amount and the interval makes it feasible to control the distribution of quantum dots within a silica particle.

When the divided amount is too small, no division effect results and similarly to the conventional method, quantum dots are concentrated in the central portion of the silica particle, rendering it difficult to achieve effects of the present invention. When a divided amount is too large, the progress of hydrolysis of a silicon-containing alkoxide compound becomes non-homogeneous, resulting in increased scattering in silica nanoparticle size.

When an addition interval is too short, no division effect results and similarly to the conventional method, quantum dots are concentrated in the central portion of the silica particle, rendering it difficult to achieve effects of the present invention. When an addition interval is too long, the progress of hydrolysis of a silicon-containing alkoxide compound becomes non-homogeneous, resulting in increased scattering of silica nanoparticle size.

The reaction time in the step (3), which may be conditions applicable to hydrolysis of conventional silicon-containing alkoxide compounds, is preferably not less than 3 hours and not more than 50 hours. A shorter time than this renders it difficult to complete the reaction, leading to a lowering of yield. Whereas, a longer time than this leads to excessive progress of the reaction, resulting in formation of insoluble matter.

Recovery of the formed quantum dot-embedding silica nanoparticles from the reaction mixture in the step (4) can employ filtration or centrifugal separation which is conventionally conducted in recovery of nanoparticles. The thus recovered quantum dot-embedded silica nanoparticles may optionally be washed with an organic solvent or water to remove unreacted raw materials or the like.

Organic Molecule Modification:

A biosubstance labeling agent related to the present invention comprises a quantum dot-embedded silica nanoparticle and a molecular labeling material which are bound through an organic molecule. The binding mode is not specifically limited and includes, for example, a covalent bond, an ionic bond, a hydrogen bond, a coordination bond, chemical absorption and physical absorption. Of these, a strong bond such as a covalent bond is preferred in terms of boding stability.

As a compound capable of bonding to the surface of a quantum dot-embedded silica nanoparticle is usable a silane coupling agent which is broadly employed as a compound capable of boding an organic compound to an inorganic compound. Such a silane coupling agent is a compound which contains, on one end of the molecule, an alkoxysilyl group capable of forming a silanol group upon hydrolysis and, on the other end, a functional group such as a mercapto group (thiol group), a carboxyl group, an amino group, an epoxy group, or an aldehyde group, and is capable of bonding to an inorganic compound through an oxygen atom of the foregoing silanol group. Specific examples of a silane coupling agent include mercaptopropyltriethoxysilane, aminopropyltriethoxysilane and the like.

In cases when using such a silane coupling agent as a biosubstance labeling agent, there is usable a silane coupling agent containing a polyethylene chain to inhibit nonspecific adsorption to a biosubstance (for example, PEG-silane no. SIM 6492.7, produced by Gelest Corp.). Two or more silane coupling agents may be used in combination.

The reaction of a quantum dot-embedded silica nanoparticle and a silane coupling agent can be performed according to the procedure known in the art. For instance, quantum dot-embedded silica nanoparticles are dispersed in pure water, then, aminopropyltriethoxysilane is added thereto and allowed to react over 12 hours. After completing the reaction, quantum dot-embedded silica nanoparticles which have been surface-modified with an aminopropyl group are obtained through centrifugal separation or filtration.

Biosubstance Labeling Agent:

The biosubstance labeling agent related to the present invention can be obtained by allowing the foregoing quantum dot-embedded silica nanoparticle and a molecular labeling substance to be bound through an organic molecule.

In the biosubstance labeling agent related to the present invention, a molecular labeling substance specifically binds to and/or reacts with a targeted biosubstance, rendering it feasible to label the biosubstance.

Examples of such a molecular labeling substance include a nucleotide chain, a protein and an antibody.

For example, an amino group of a quantum dot-embedded silica nanoparticle which has been modified with aminopropyltriethoxysilane and a carboxyl group of an antibody are reacted, whereby the antibody can be bonded to the quantum dot-embedded silica nanoparticle through an amide bond. There may optionally be used a condensation agent such as EDC (1-Ethyl-3-[3-Dimethylaminopropyl]carbodiimide hydrochloride, produced by Pierce Corp.).

There may optionally be used a linker compound having a site capable of direct-binding to a quantum dot-embedded silica nanoparticle and a site capable of binding to a molecular targeted substance. Specifically, using sulfo-SMCC (Sulfosuccinimidyl 4[N-maleimidomethyl]-cyclohexane-1-carboxylate, produced by Pierce Corp.), an amino group of a quantum dot-embedded silica nanoparticle which has been modified with aminopropyltriethoxysilane and a mercapto group of an antibody are bonded to form a quantum dot-embedded silica nanoparticle having an bonded antibody.

EXAMPLES

Hereinafter, the present invention is described in detail with reference to examples, but the invention is by no means limited thereto.

Ratio of the number of quantum dots existing in a concentric area within 10% of a radius from the center of the silica nanoparticle to the number of total quantum dots embedded:

when taking a photograph of a quantum dot-embedded silica nanoparticle by a transmission electron microscope (TEM), a quantum dot and silica are different in transmittance of an electron beam, so that the quantum dot and the silica portion are observed black and white, respectively.

This is also supported by energy dispersive X-ray analysis (EDS). Specifically, when a white portion observed in a TEM image is subjected to EDS, peaks derived from silicon and oxygen are observed. On the other hand, when a black portion observed in a TEM image is subjected to EDS, a peak derived from a quantum dot, in addition to silicon and oxygen, was observed. More specifically, in cases when using CdSe/ZnS as a quantum dot, peaks of cadmium, selenium, zinc and sulfur are observed.

In a TEM image of a silica nanoparticle, all of areas of black portions observed are summed, which is denoted as value (I). Subsequently, the area of black portions existing in a concentric area within 10% of a radius from the center of the silica nanoparticle is determined as an area value (II). The value of the value (II) divided by value (I) and multiplied by 100 is defined as the ratio of the number of quantum dots existing in a concentric area within 10% of a radius from the center of the silica nanoparticle to the total number of quantum dots embedded within the silica nanoparticle. In the present invention, this ratio is determined with respect to 1000 particles and its arithmetic average was employed.

Example 1

CdSe/ZnS Embedded Silica Nanoparticle

CdSe/ZnS embedded silica nanoparticles were prepared by the process comprising the following steps (1) to (4).

Step (1):

There were mixed 10 µl of CdSe/ZnS decane dispersion (Invitrogen Corp., Q dot trademark 655) and 40 µl of tetraethoxysilane.

Step (2):

There were mixed 4 ml of ethanol and 1 ml of 14% ammonia water.

Step (3):

The mixture prepared in the step (2) was divided into five portions, which were added at intervals of 10 minutes to the mixture prepared in the step (2), while being stirred. Stirring was conducted over 12 hours from the start of stirring.

Step (4):

The obtained reaction mixture of 10000 g was subjected to centrifugal separation over 60 minutes to remove the supernatant. Further, ethanol was added thereto, precipitates were dispersed and the dispersion was again subjected to centrifugal separation. Then, washing with ethanol and water was conducted in the same procedure as above.

The thus obtained CdSe/ZnS-embedded silica nanoparticles were observed by an SEM and it was proved that the average particle size and the coefficient of variation were 200 nm and 7%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 15%.

Example 2

CdSe/ZnS Embedded Silica Nanoparticle

CdSe/ZnS embedded silica nanoparticles were prepared by the process comprising the following steps (1) to (3).

Step (1):

There were mixed 10 µl of CdSe/ZnS decane dispersion (Invitrogen Corp., Q dot trademark 655) and 40 µl of tetraethoxysilane.

Step (2)

There were mixed 4 ml of ethanol and 1 ml of 14% ammonia water.

Step (3):

The mixture prepared in the step (2) was divided to five portions, which were added at intervals of 20 minutes to the mixture prepared in the step (2), while being stirred.

Further, operations were conducted in the same manner as in Example 1.

The thus obtained CdSe/ZnS-embedded silica nanoparticles were observed by an SEM and it was proved that the average particle size and the coefficient of variation were 190 nm and 10%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 40%.

Example 2-2

CdSe/ZnS Embedded Silica Nanoparticle

CdSe/ZnS embedded silica nanoparticles were prepared by the process comprising the following steps (1) to (3).
Step (1):
There were mixed 10 µl of CdSe/ZnS decane dispersion (Invitrogen Corp., Q dot trademark 655) and 40 µl of tetraethoxysilane.
Step (2)
There were mixed 4 ml of ethanol and 1 ml of 14% ammonia water.
Step (3):
The mixture prepared in the step (2) was divided to eight portions, which were added at intervals of 15 minutes to the mixture prepared in the step (2), while being stirred. Stirring was conducted over 12 hours from the start of stirring.

Further, operations were conducted in the same manner as in Example 1.

The thus obtained CdSe/ZnS-embedded silica nanoparticles were observed by an SEM and it was proved that the average particle size and the coefficient of variation were 210 nm and 9%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 10%.

Example 2-3

CdSe/ZnS Embedded Silica Nanoparticle

CdSe/ZnS embedded silica nanoparticles were prepared by the process comprising the following steps (1) to (3).
Step (1):
There were mixed 10 µl of CdSe/ZnS decane dispersion (Invitrogen Corp., Q dot trademark 655) and 40 µl of tetraethoxysilane.
Step (2)
There were mixed 4 ml of ethanol and 1 ml of 14% ammonia water.
Step (3):
The mixture prepared in the step (2) was divided to three portions, which were added at intervals of 15 minutes to the mixture prepared in the step (2), while being stirred. Stirring was conducted over 12 hours from the start of stirring.

Further, operations were conducted in the same manner as in Example 1.

The thus obtained CdSe/ZnS-embedded silica nanoparticles were observed by an SEM and it was proved that the average particle size and the coefficient of variation were 210 nm and 9%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 70%.

Comparative Example 1

CdSe/ZnS Embedded Silica Nanoparticle

In accordance with the method described in the afore-described Patent document 2 were mixed 10 µl of CdSe/ZnS decane dispersion (Invitrogen Corp., Q dot trademark 655), 40 µl of tetraethoxysilane and ethanol. To this mixture was added 1 ml of 14% ammonia water at one time, while stirring.

After stirring continued over 12 hours under room temperature, operations were conducted in the same manner as in Example 1.

The thus obtained CdSe/ZnS-embedded silica nanoparticles were observed by an SEM and it was proved that the average particle size and the coefficient of variation were 180 nm and 9%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 85%.

Comparative Example 2

CdSe/ZnS Embedded Silica Nanoparticle

CdSe/ZnS embedded silica nanoparticles were prepared by the process comprising the steps of (1) to (3), as described below.
Step (1):
There were mixed 10 µl of CdSe/ZnS decane dispersion (Invitrogen Corp., Q dot trademark 655) and 40 µl of tetraethoxysilane.
Step (2):
There were mixed 4 ml of ethanol and 1 ml of 14% ammonia water.
Step (3):
The mixture prepared in the step (2) was divided to fifty portions, which were added at intervals of 30 minutes to the mixture prepared in the step (2), while being stirred.

Further, operations were conducted in the same manner as in Example 1.

The thus obtained CdSe/ZnS-embedded silica nanoparticles were observed by an SEM and it was proved that the average particle size and the coefficient of variation were 200 nm and 25%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 5%.

Example 3

InGaP/ZnS Embedded Silica Nanoparticle

InGaP/ZnS embedded silica nanoparticles were prepared by the process comprising the steps of (1) to (3), as described below.
Step (1):
There were mixed 10 µl of an aqueous dispersion of InGaP/ZnS having a carboxyl group on the surface [eBioscience Corp., eFluot trademark 700NC (carboxyl)] and 40 µl of tetraethoxysilane.

Step (2):

There were mixed 4 ml of ethanol and 1 ml of 14% ammonia water.

Step (3):

The mixture prepared in the step (2) was divided into five portions, each of which was added at intervals of 10 minutes to the mixture prepared in the step (2), while being stirred.

Further, operations were conducted in the same manner as in Example 1.

The thus obtained InGaP/ZnS-embedded silica nanoparticles were observed by an SEM and it was proved that the average particle size and the coefficient of variation were 140 nm and 8%, respectively. As a result of observation by a TEM, it was proved that the ratio of the number of quantum dots existing in a concentric area within 10% of the radius from the center of a silica nanoparticle to the total number of quantum dots embedded within the silica nanoparticle was 25%.

Example 3-2

InGaP/ZnS Embedded Silica Nanoparticle

InGaP/ZnS embedded silica nanoparticles were prepared by the process comprising the steps of (1) to (3), as described below.

Step (1):

There were mixed 10 μl of an aqueous dispersion of InGaP/ZnS having a carboxyl group on the surface [eBioscience Corp., eFluor trademark 700NC (carboxyl)] and 40 μl of tetraethoxysilane.

Step (2):

There were mixed 4 ml of ethanol and 1 ml of 14% ammonia water.

Step (3):

The mixture prepared in the step (2) was divided to three portions, each of which was added at intervals of 5 minutes to the mixture prepared in the step (2), while being stirred.

Further, operations were conducted in the same manner as in Example 1.

The thus obtained InGaP/ZnS-embedded silica nanoparticles were observed by an SEM and it was proved that the average particle size and the coefficient of variation were 160 nm and 5%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 70%.

Comparative Example 3

Preparation of InGaP/ZnS Embedded Silica Nanoparticle

In accordance with the method described in the aforedescribed Patent document 2 were mixed 10 μl of an aqueous dispersion of InGaP/ZnS having a carboxyl group on the surface [eBioscience Corp., eFluor trademark 700NC (carboxyl)], 10 μl of tetraethoxysilane and 4 ml of ethanol. To this mixture was added 1 ml of 14% ammonia water at one time, while stirring.

After stirring over 12 hours under room temperature, operations were conducted in the same manner as in Example 1.

The thus obtained InGaP/ZnS-embedded silica nanoparticles were observed by an SEM and it was proved that the average particle size and the coefficient of variation were 180 nm and 10%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 90%.

Example 4

Si Embedded Silica Nanoparticle

Si quantum dots were prepared by HF etching of silicon wafer, disclosed in JP 2005-172429 A.

Step (1):

There was prepared a mixture of 10 μl of an aqueous Si quantum dot dispersion and 40 μl of tetraethoxysilane.

Step (2):

There was prepared a mixture of 4 ml of ethanol and 1 ml of a 14% ammonia water.

Step (3):

The mixture prepared in the step (1) was divided to five parts, each of which was added at intervals of 20 minutes to the mixture prepared in the step (2) with stirring under room temperature.

Further, operations were conducted in the same manner as in Example 1.

The thus obtained Si-embedded silica nanoparticles were observed by an SEM and it was proved that the average particle size and the coefficient of variation were 250 nm and 6%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 55%.

Comparative Example 4

Si Embedded Silica Nanoparticle

In accordance with the method described in the aforedescribed Patent document 2 were mixed 10 μl of an aqueous Si quantum dot dispersion, 40 μl of tetraethoxysilane and 4 ml of ethanol. Further thereto, 1 ml of a 14% ammonia water was added with stirring.

After stirring over 12 hours under room temperature, operations were conducted in the same manner as in Example 1.

The thus obtained Si-embedded silica nanoparticles were observed by an SEM and it was proved that the average particle size and the coefficient of variation were 280 nm and 9%, respectively. As a result of observation by a TEM, it was proved that the ratio of the number of quantum dots existing in a concentric area within 10% of a radius from the center of a silica nanoparticle to the total number of quantum dots embedded within the silica nanoparticle was 80%.

The thus obtained quantum dot embedded silica nanoparticles were dispersed in 5 ml of pure water and subjected to fluorometry. Fluorescence intensity was represented by a relative value, based on the fluorescence intensities of CdSe/ZnS embedded silica nanoparticles obtained in Example 1, InGaP/ZnS embedded silica nanoparticles obtained in Example 3, and Si embedded silica nanoparticles obtained in Example 4, each being 100. Evaluation results are shown Tables 1 to 3.

TABLE 1

|  | Example 1 | Example 2 | Comparative Example 1 | Comparative Example 2 |
|---|---|---|---|---|
| Quantum Dot | CdSe/ZnS | CdSe/ZnS | CdSe/ZnS | CdSe/ZnS |
| Silica Nanoparticle Size (nm) | 200 | 190 | 180 | 200 |
| Ratio of Number of Quantum Dots existing within 10% of radius from the center (%) | 15 | 40 | 85 | 5 |
| Fluorescence Intensity | 100 | 110 | 70 | 60 |

TABLE 2

|  | Example 3 | Comparative Example 3 |
|---|---|---|
| Quantum Dot | InGaP/ZnS | InGaP/ZnS |
| Silica Nanoparticle Size (nm) | 140 | 180 |
| Ratio of Number of Quantum Dots existing within 10% of radius from the center (%) | 25 | 90 |
| Fluorescence Intensity | 100 | 65 |

TABLE 3

|  | Example 4 | Comparative Example 4 |
|---|---|---|
| Quantum Dot | Si | Si |
| Silica Nanoparticle Size (nm) | 250 | 280 |
| Ratio of Number of Quantum Dots existing within 10% of radius from the center (%) | 55 | 80 |
| Fluorescence Intensity | 100 | 75 |

As is apparent from Tables 1 to 3, it was shown that silica nanoparticles, in which the ratio of the number of quantum dots existing in a concentric area within 10% of a radius from the center of a silica nanoparticle to the total number of quantum dots embedded within the silica nanoparticle was not less than 80%, resulted in reduced fluorescence intensity. This is presumed to be due to quantum dots being concentrated around the center of a silica nanoparticle, causing quenching.

On the contrary, it was also shown that when the ratio of the number of quantum dots existing in a concentric area within 10% of a radius from the center of a silica nanoparticle to the total number of quantum dots embedded within the silica nanoparticle is extremely low, the fluorescence intensity was also low. In that case, it is assumed that quantum dots are unevenly distributed near the circumference of a silica nanoparticle, causing quenching.

From the foregoing results, it is proved that an enhanced emission intensity of quantum dot-embedded silica nanoparticles of the present invention is due to the fact that quantum dots are evenly distributed throughout the entire silica nanoparticle.

Example 5

Organic Molecular Modification of CdSe/ZnS Embedded Silica Nanoparticle

In 5 ml of pure water was dispersed 1 mg of CdSe/ZnS embedded silica nanoparticles. Further thereto was added 100 µl of an aqueous solution of aminopropyltriethoxysilane and stirred over 12 hours at room temperature.

Then, the reaction mixture was subjected to centrifugal separation under 10000 g and the supernatant was removed. Further thereto, ethanol was added and precipitates were dispersed, and the dispersion was again subjected to centrifugal separation. Further, washing with ethanol and pure water was conducted in the same manner as above.

When the thus obtained amino group-modified CdSe/ZnS embedded silica nanoparticles were subjected FT-IR spectrometry, an absorption derived from an amino group was observed, whereby amino group modification was confirmed.

In 5 ml pure water was dispersed 1 mg of amino group-modified CdSe/ZnS embedded silica nanoparticles and subjected to fluorophotometry and it was confirmed that fluorescence intensity before reaction was maintained.

Example 6

Bonding of Antibody to Amino Group-Modified CdSe/ZnS Embedded Silica Nanoparticle To 2 ml of DMSO was added 0.1 ml of a dispersion in which 0.5 mg of amino group-modified CdSe/ZnS embedded silica nanoparticles obtained in Example 5 was dispersed in 0.5 ml of pure water. Further thereto, sulfo-SMCC (produced by Piece Corp.) was added and reacted. Excess sulfo-SMCC was removed by centrifugal separation, while anti-hCG antibody was subjected to a reduction treatment with 1 M dithiothreiytol (DTT) and excess DTT was removed through a gel filtration column.

The CdSe/ZnS embedded silica nanoparticles which were treated with sulfo-SMCC and the anti-hCG antibody which was treated with DTT were mixed and allowed to react over 1 hour. Then, 10 mM mercaptoethanol was added thereto to terminate the reaction. Unreacted materials were removed through a gel filtration column, whereby CdSe/ZnS embedded silica nanoparticles with attached anti-hCG antibody were obtained.

In 0.5 ml pure water were dispersed 0.1 mg of CdSe/ZnS embedded silica nanoparticles with attached anti-hCG antibody and subjected to fluorophotometry and a fluorescence intensity before reaction was confirmed to be maintained.

An immunoassay using the thus obtained CdSe/ZnS embedded silica nanoparticles with attached anti-hCG antibody was conducted according the procedure described below.
1) Anti-hα subnit is fixed in a well on a microplate,
2) hCG as antigen is placed into each of wells with varying concentration,
3) excess hCG is removed by washing and then, a dispersion of CdSe/ZnS embedded silica nanoparticles with attached anti-hCG antibody is added to each of the wells,
4) Excess CdSe/ZnS embedded silica nanoparticles with attached anti-hCG antibody are removed by washing, and
5) The fluorescence intensity of each well is measured by a microplate reader.

As a result of the foregoing immunoassay, fluorescence intensity was increased in response to the antigen concentration. Namely, anti-hCG antibody attached to CdSe/ZnS embedded silica nanoparticles is not vitiated in antigen recognition capability. Thus, according to this result, it is proved that there can be provided a biosubstance labeling agent using quantum dot-embedded silica nanoparticles.

What is claimed is:
1. A quantum dot-embedded silica nanoparticle having plural quantum dots embedded within the silica nanoparticle, wherein the number of quantum dots existing in a concentric area within 10% of a radius from a center of the silica nanoparticle accounts for 10 to 70% of the number of total quantum dots embedded in the silica nanoparticle.

2. The quantum dot-embedded silica nanoparticle, as claimed in claim 1, wherein the number of quantum dots existing in a concentric area within 10% of a radius from a center of the silica nanoparticle accounts for 15 to 55% of the number of total quantum dots embedded in the silica nanoparticle.

3. The quantum dot-embedded silica nanoparticle, as claimed in claim 2, wherein the number of quantum dots existing in a concentric area within 10% of a radius from a center of the silica nanoparticle accounts for 30 to 50% of the number of total quantum dots embedded in the silica nanoparticle.

4. The quantum dot-embedded silica nanoparticle, as claimed in claim 1, wherein the quantum dots comprise any one of a II-VI group compound, a III-V group compound and a IV group element.

5. The quantum, dot-embedded silica nanoparticle, as claimed in claim 1, wherein the quantum dots comprise InP or InGaP.

6. The quantum dot-embedded silica nanoparticle, as claimed in claim 1, wherein the quantum dots comprise Si.

7. The quantum dot-embedded silica nanoparticle, as claimed in claim 1, wherein a surface of the silica nanoparticle is modified with an organic molecule.

8. A method of producing a quantum dot-embedded silica nanoparticle, as claimed in claim 1, the method comprising the steps of:
(a) mixing a silicon-containing alkoxide compound and quantum dots to prepare a quantum dot-containing solution,
(b) mixing an organic solvent, water and a base to prepare a mixed solution, and
(c) dividing the quantum dot-containing solution prepared in the step (a) to parts and adding each of the parts intermittently to the mixed solution prepared in the step (b) with stirring to perform reaction.

9. A biosubstance labeling agent comprising:
a silica nanoparticle;
a plurality of quantum dots embedded within the silica nanoparticle, a number of quantum dots existing in a concentric area within 10% of a radius from a center of the silica nanoparticle accounts for 15 to 55% of the number of total quantum dots embedded in the silica nanoparticle; and
a molecular labeling substance bonded to the quantum dots embedded silica nanoparticle through an organic molecule.

10. The biosubstance labeling agent, as claimed in claim 9, wherein the number of quantum dots existing in a concentric area within 10% of a radius from a center of the silica nanoparticle accounts for 30 to 50% of the number of total quantum dots embedded in the silica nanoparticle.

11. The biosubstance labeling agent, as claimed in claim 9, wherein the quantum dots comprise any one of a II-VI group compound, a III-V group compound and a IV group element.

12. The biosubstance labeling agent, as claimed in claim 9, wherein the quantum dots comprise InP or InGaP.

13. The biosubstance labeling agent, as claimed in claim 9, wherein the quantum dots comprise Si.

14. The biosubstance labeling agent, as claimed in claim 9, wherein a surface of the quantum dots-embedded silica nanoparticle is modified with the organic molecule.

15. The biosubstance labeling agent, as claimed in claim 9, wherein the quantum dots have an average particle size of 2 to 10 nm and the quantum dots-embedded silica nanoparticle has an average particle size of in a range of 30 to 800 nm and a coefficient of variation of particle size is in a range of not more than 20%.

16. A method of producing the biosubstance labeling agent, as claimed in claim 9, comprising the steps of:
(a) mixing a silicon-containing alkoxide compound and quantum dots to prepare a quantum dot-containing solution,
(b) mixing an organic solvent, water and a base to prepare a mixed solution;
(c) dividing the quantum dot-containing solution prepared in the step (a) into parts and adding each of the parts intermittently to the mixed solution prepared in the step (b) with stirring to perform a reaction and form silica nanoparticles having embedded quantum dots;
(d) modifying the quantum dots-embedded silica nanoparticles with the organic molecule; and
(e) bonding a biosubstance labeling agent to the modified quantum dots-embedded silica nanoparticle through the organic molecule.

* * * * *